United States Patent
Ferritto et al.

(10) Patent No.: US 10,219,992 B2
(45) Date of Patent: Mar. 5, 2019

(54) COSMETIC COMPOSITION COMPRISING HYDROPHILIC ORGANOSILANES

(71) Applicant: Dow Corning Corporation, Midland, MI (US)

(72) Inventors: Michael Salvatore Ferritto, Midland, MI (US); Lenin James Petroff, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 197 days.

(21) Appl. No.: 15/343,623

(22) Filed: Nov. 4, 2016

(65) Prior Publication Data
US 2017/0071847 A1 Mar. 16, 2017

Related U.S. Application Data

(62) Division of application No. 14/068,536, filed on Oct. 31, 2013, now abandoned.

(60) Provisional application No. 61/721,688, filed on Nov. 2, 2012.

(51) Int. Cl.
| | |
|---|---|
| A61K 8/894 | (2006.01) |
| A61Q 5/12 | (2006.01) |
| A61Q 19/00 | (2006.01) |
| C08G 65/26 | (2006.01) |
| A61Q 5/00 | (2006.01) |
| A61Q 5/06 | (2006.01) |

(52) U.S. Cl.
CPC ............ *A61K 8/894* (2013.01); *A61Q 5/12* (2013.01); *A61Q 19/00* (2013.01); *C08G 65/2639* (2013.01); *A61Q 5/004* (2013.01); *A61Q 5/06* (2013.01)

(58) Field of Classification Search
None
See application file for complete search history.

(56) References Cited

U.S. PATENT DOCUMENTS

| | | |
|---|---|---|
| 6,191,220 B1 | 2/2001 | Takei et al. |
| 6,228,968 B1 | 5/2001 | Yoshioka et al. |

FOREIGN PATENT DOCUMENTS

| | | |
|---|---|---|
| DE | 2426698 | 11/1975 |
| JP | 09-104833 | 4/1997 |
| JP | 10059828 | 3/1998 |
| JP | 2003-26958 | 1/2003 |
| WO | 2013066911 | 5/2013 |

OTHER PUBLICATIONS

JP09-104833, Machine Translation.
JP2003-26958, Machine Translation.
Akimoto et al.: "Polymeric percutaneous drug penetration enhancer—Synthesis and enhancing property of PEG/PDMS block copolymer with a cationic end group", Jouranl of Controlled Release, Elsevier, Amsterdam, NL, vol. 49, No. 2-3, Dec. 15, 1997, pp. 229-241.
Boksanyi et al.: "Chemically modified silicon dioxide surfaces reaction of N-Alkyldimethylsilanols and N-Oxaalkyl-Dimethylsilanols with the hydrated surface of silicon-dioxide—the qauestion of the limited surface concentration", Advances in Colloid and Interface Science, vol. 6, Jan. 1, 1976, pp. 95-137.
Sabourault et al.: "Platinum oxide (PTO(2)): A potent hydrosilylation catalyst", Organic Letters, American Chemical Society, US, vol. 4, No. 13, Jun. 27, 2002, pp. 2117-2119.
Boksanyi et al.: "Note on the Preparation of Alkyl= and Oxaalkyl-dimethylsilanols", Helvetica Chimica Acta, Verlag Helvetica Chimica Acta, Basel, Ch, vol. 59, No. 3, Jan. 1, 1976, pp. 717-727.
Machine translation of JP10059828, Jan. 15, 2016.

*Primary Examiner* — Mina Haghighatian
*Assistant Examiner* — Luke E Karpinski
(74) *Attorney, Agent, or Firm* — Catherine U. Brown

(57) ABSTRACT

The present disclosure relates to cosmetic compositions comprising an organosilane (A) having the formula:

$$(R^1)_n(R^2O)_{(3-n)}SiR^3O(CH_2CH_2O)_a(C_3H_6O)_bR^4$$

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group;
and a cosmetic ingredient (B), and optionally in a cosmetically acceptable medium.

13 Claims, No Drawings

COSMETIC COMPOSITION COMPRISING HYDROPHILIC ORGANOSILANES

CROSS REFERENCE TO RELATED APPLICATIONS

This application is a divisional of and claims the benefit of U.S. patent application Ser. No. 14/068,536, filed on Oct. 31, 2013 which is a non-provisional of and claims priority benefit of U.S. Provisional Patent Application No. 61/721, 688 filed Nov. 2, 2012, the entire content of which is incorporated herein by reference.

TECHNICAL FIELD

This disclosure relates to cosmetic compositions comprising an organosilane (A) containing a polyoxyalkylene moiety, and at least one cosmetic ingredient (B), in a cosmetically acceptable medium.

BACKGROUND OF THE INVENTION

Organosilanes have been used in cosmetic applications to provide for various benefits, such as hydration, hair conditioning, foam boosting, humectancy.

Organosilanes may be used to treat pigments or filler surfaces for compatibilization, dispersibility, wettability. Organosilanes may also be used as surface active ingredient to form emulsions, such as water-in-oil or oil-in-water emulsions.

Skin hydration is a critical parameter in delaying the signs of skin ageing. Therefore, appropriate actives are included in cosmetic and dermatological compositions, aimed at compensating for dehydration of skin by increasing the water content in the upper layers of the skin. Various mechanisms exist such as increasing the amount of water in the upper layers of the skin with actives such as polyols and specifically glycerin, glycols, and sugars; or preventing water from evaporating by forming a so-called barrier, usually in the form of a hydro-lipidic film.

Polyols have the major drawback of being tacky at some higher levels, and only provide hydration for a period not longer than a day.

Barrier ingredients such as petrolatum have only a delayed effect, where hydration retention starts only after several hours.

There is an ongoing need for actives which provide for immediate and longer lasting hydration to the skin, and which do not negatively impact the sensory profile of the cosmetic or dermatological product.

BRIEF SUMMARY

The present invention relates to cosmetic compositions comprising organosilanes containing a polyoxyalkylene moiety. In particular, the present disclosure relates to cosmetic compositions comprising an organosilane (A) having the formula;

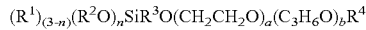

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group.
and at least one cosmetic ingredient (B).

DETAILED DESCRIPTION

The present invention relates to compositions comprising an organosilane (A), or reaction products therefrom, having the formula;

where
n is 1, 2, or 3, alternatively n is 2, a≥1, 0≤b≤30, with the proviso that a≥b,
$R^1$ is a hydrocarbon group containing 1 to 12 carbon atoms, alternatively $R^1$ is an alkyl group or a phenyl group, alternatively $R^1$ is methyl,
$R^2$ is hydrogen or an alkyl group contain 1 to 6 carbon atoms, alternatively $R^2$ is methyl or ethyl, alternatively $R^2$ is ethyl,
$R^3$ is a divalent hydrocarbon group containing 2 to 12 carbon atoms, alternatively $R^3$ contains 2 to 6 carbon atoms, alternatively $R^3$ is propylene, or isobutylene, alternatively $R^3$ is —CH$_2$CH$_2$C(CH$_3$)$_2$—, alternatively $R^3$ is propylene,
$R^4$ is hydrogen, $R^1$, or an acetyl group, alternatively $R^4$ is methyl;
and at least one cosmetic ingredient (B), in a cosmetically acceptable medium.

Organosilane (A) contains a polyoxyalkylene moiety which is predominantly a polyoxyethylene chain as designated by (CH$_2$CH$_2$O)$_a$ in the above formula. The polyoxyalkylene group comprises predominately oxyethylene units (C$_2$H$_4$O), but may also contain oxypropylene units (C$_3$H$_6$O), oxybutylene units (C$_4$H$_8$O), or mixtures thereof. When the polyoxyalkylene group comprises a mixture of (C$_2$H$_4$O), (C$_3$H$_6$O), and/or (C$_4$H$_8$O) units, the oxyalkylene groups are typically randomized within the group but can also be blocked. Typically, the polyoxyalkylene group comprises a majority of polyoxyethylene units, as defined on a molar basis and indicated in the above formula by the "a" subscript.

The subscript "a" is equal to or greater than 1,
alternatively a may vary from 4 to 30,
    alternatively a may vary from 4 to 20,
        alternatively a may vary from 4 to 10,
            alternatively a may vary from 5 to 8,
                alternatively a is 7.
The subscript "b" varies from 0 to 30,
alternatively b may vary from 1 to 30,
    alternatively a may vary from 1 to 20,
        alternatively a may vary from 10 to 20,
            alternatively a may vary from 15 to 20,
with the proviso that a≥b.
In one embodiment, the organosilane (A) has the following average formula:

In one embodiment, the organosilane (A) has the following average formula:

The organosilanes (A) may be prepared by any method known in the art for preparing organosilanes, or alternatively the organosilanes (A) may be prepared by the process as discussed below.

The organosilane (A) may be prepared by a process comprising reacting:
a) an organosilane of the formula $(R^1)_{(3-n)}(R^2O)_n SiH$,
    where $R^1$ is a hydrocarbon group containing 1 to 12 carbon atoms,
    $R^2$ is hydrogen or an alkyl group contain 1 to 6 carbon atoms,
    the subscript n is 1, 2, or 3, alternatively n is 2,
b) a polyoxyalkylene of the formula $R^5O(CH_2CH_2O)_a(C_3H_6O)_b R^4$
    where the subscript "a" is equal to or greater than 1,
    the subscript "b" varies from 0 to 30,
        with the proviso that a≥b,
    $R^4$ is hydrogen, $R^1$, or an acetyl group,
    $R^5$ is an unsaturated aliphatic hydrocarbon group containing 2 to 12 carbon atoms, and
c) a hydrosilylation catalyst.

Component a) is an organosilane of the formula $(R^1)_{(3-n)}(R^2O)_n SiH$. Alternately, it is possible for two or more H groups to be present on the Si atom, in which case $R^1$ would be zero. In cases such as this, two polyether groups would subsequently be grafted onto the Si atom. Representative examples of organosilanes suitable as component a) in the present process include;

$(CH_3)(CH_3CH_2O)_2SiH$, $(CH_3)(CH_3O)_2SiH$, $(CH_3CH_2)(CH_3CH_2O)_2SiH$, $(CH_3CH_2)(CH_3O)_2SiH$ $(CH_3)(HC(CH_3)_2O)_2SiH$ $(CH_3CH_2O)_2SiH_2$

The polyoxyalkylene useful as component b) can be any polyoxyalkylene that is terminated at one molecular chain end with an unsaturated aliphatic hydrocarbon group containing 2 to 12 carbon atoms. The polyoxyalkylene may result from the polymerization of ethylene oxide, propylene oxide, butylene oxide, 1,2-epoxyhexane, 1,2-epoxyoctane, cyclic epoxides such as cyclohexene oxide or exo-2,3-epoxynorborane. The polyoxyalkylene group comprises predominately oxyethylene units ($C_2H_4O$), but may also contain minor amounts of oxypropylene units ($C_3H_6O$), oxybutylene units ($C_4H_8O$), or mixtures thereof. Typically, the polyoxyalkylene group comprises a majority of oxyethylene units, as defined on a molar basis and indicated in the above formula by the "a" subscript. When present, the oxypropylene units are indicated in the above formula by the "b" susbscript. The unsaturated aliphatic hydrocarbon group can be an alkenyl or alkynyl group. Representative, non-limiting examples of the alkenyl groups are shown by the following structures; $H_2C=CH—$, $H_2C=CHCH_2—$, $H_2C=CHC(CH_3)_2—$, $H_2C=C(CH_3)CH_2—$, $H_2C=CHCH_2CH_2—$, $H_2C=CHCH_2CH_2CH_2—$, and $H_2C=CHCH_2CH_2CH_2CH_2—$. Representative, non-limiting examples of alkynyl groups are shown by the following structures; $HC≡C—$, $HC≡CCH_2—$, $HC≡CCH(CH_3)—$, $HC≡CC(CH_3)_2—$, and $HC≡CC(CH_3)_2CH_2—$.

Polyoxyalkylenes having an unsaturated aliphatic hydrocarbon group at one molecular terminal are known in the art, and many are commercially available. Representative, non-limiting examples of polyoxyalkylenes having an unsaturated aliphatic hydrocarbyl at one molecular terminal include;

$H_2C=CHCH_2O[C_2H_4O]_a H$ $H_2C=CHCH_2O[C_2H_4O]_a[C_3H_6O]_b H$ $H_2C=CHCH_2O[C_2H_4O]_a CH_3$ $H_2C=CHC(CH_3)_2O[C_2H_4O]_a CH_3$ $H_2C=CHC(CH_3)_2O[C_2H_4O]_a[C_3H_6O]_b H$ $H_2C=CHCH_2O[C_2H_4O]_a C(O)CH_3$ $H_2C=C(CH_3)CH_2O[C_2H_4O]_a H$ $HC≡CCH_2O[C_2H_4O]_a H$ $HC≡CC(CH_3)_2O[C_2H_4O]_a H$ where a and b are as defined above.

Polyoxyalkylenes having an unsaturated aliphatic hydrocarbon group at one molecular terminal are commercially available from numerous suppliers including; NOF (Nippon Oil and Fat, Tokyo, Japan), Clariant Corp. (Switzerland), and Dow Chemical Corp. (Midland, Mich.). Commercial examples of these materials include Uniox MUS-4 from NOF, Polyglykol AM 450 from Clariant, and SF 400 and SF 443 from Dow.

The amounts of components a) and b) used in the hydrosilylation reaction may vary. The molar ratio of the SiH units of component a) to the aliphatic unsaturated groups of component b) may range from 10/1 to 1/10, alternatively from 5/1 to 1/5, or alternatively from 1/1 to 1/2. Typically, the amounts of components a) and b) are selected to provide molar excess of the unsaturated groups of component b) to the SiH groups in component a).

Component c) is a hydrosilylation catalyst. The hydrosilylation catalyst may be any suitable Group VIII metal based catalyst selected from a platinum, rhodium, iridium, palladium or ruthenium. Group VIII group metal containing catalysts useful to catalyze curing of the present compositions can be any of those known to catalyze reactions of silicon bonded hydrogen atoms with silicon bonded unsaturated hydrocarbon groups. The preferred Group VIII metal for use as a catalyst to effect cure of the present compositions by hydrosilylation is a platinum based catalyst. Some preferred platinum based hydrosilylation catalysts for curing the present composition are platinum metal, platinum compounds and platinum complexes.

Suitable platinum catalysts are described in U.S. Pat. No. 2,823,218 (commonly referred to as "Speier's catalyst) and U.S. Pat. No. 3,923,705. The platinum catalyst may be "Karstedt's catalyst", which is described in Karstedt's U.S. Pat. Nos. 3,715,334 and 3,814,730. Karstedt's catalyst is a platinum divinyl tetramethyl disiloxane complex typically containing about one-weight percent of platinum in a solvent such as toluene. Alternatively the platinum catalyst may be a reaction product of chloroplatinic acid and an organosilicon compound containing terminal aliphatic unsaturation, as described in U.S. Pat. No. 3,419,593. Alternatively, the hydrosilylation catalyst is a neutralized complex of platinum chloride and divinyl tetramethyl disiloxane, as described in U.S. Pat. No. 5,175,325.

Further suitable hydrosilylation catalysts are described in, for example, U.S. Pat. Nos. 3,159,601; 3,220,972; 3,296,291; 3,516,946; 3,989,668; 4,784,879; 5,036,117; and 5,175,325 and EP 0 347 895 B1.

The hydrosilylation catalyst may be added in an amount equivalent to as little as 0.001 part by weight of elemental platinum group metal, per one million parts (ppm) of the total reaction composition. Typically, the concentration of the hydrosilylation catalyst in the reaction composition is that capable of providing the equivalent of at least 1 part per million of elemental platinum group metal. A catalyst concentration providing the equivalent of 1 to 500, alternatively 50 to 500, alternatively 50 to 200 parts per million of elemental platinum group metal may be used.

The reaction effected in the present process is a hydrosilylation reaction, wherein the SiH units of component a) react with the unsaturated aliphatic hydrocarbon group of component b) form an Si—C bond. The reaction may be conducted under those conditions known in the art for effecting hydrosilylations reactions.

The hydrosilylation reaction can be conducted neat or in the presence of a solvent. The solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent can be up to 70 weight percent, but is typically from 20 to 50 weight percent, said weight percent being based on the total weight of components in the hydrosilylation reaction. The solvent used during the hydrosilylation reaction can be subsequently removed from the resulting organosilane by various known methods.

Additional components can be added to the hydrosilylation reaction which are known to enhance such reactions. These components include salts such as sodium acetate which have a buffering effect in combination with platinum catalysts.

The organosilane (A) contains at least one alkoxy group, as represented by ($R^2O$) in the formula above. As such, organosilanes (A) may hydrolyze in aqueous medium, and may further condense with itself or with other alkoxy silane or halide functional silanes, to form oligomeric or higher molecular weight polymeric siloxanes.

Thus, the present disclosure relates to the reaction products resulting from the hydrolysis and/or condensation of the aforementioned organosilanes. The organosilanes (A), or subsequently produced oligomeric or polymeric siloxanes derived from the organosilanes, may react with hydroxyl functional compounds, or surfaces or substrates such as pigments or fillers. Since the organosilanes (A) contain a polyalkylene oxide chain that is predominately ethylene oxide, the present organosilanes may be considered as "hydrophilic".

Organosilanes (A) may be used to treat various substrates to impart greater "hydrophilicity" to the substrates. Furthermore, the reactivity of the silane moiety may allow the present compositions to bond to various substrates to provide a longer lasting, more durable hydrophilic treatment.

The organosilane (A) may be used neat, as an aqueous solution, as a solution in an organic solvent. When used as a solution, additional components such as acids or bases to buffer the pH may be added to the solution which are known to enhance the hydrolysis and condensation of alkoxysilanes.

Cosmetic compositions include those compositions which are intended to be placed in contact with the external parts of the human body (skin (epidermis), hair system, nails, etc.) or with the teeth and the mucous membranes of the oral cavity with a view exclusively or mainly to cleaning them, perfuming them, changing their appearance, protecting them, keeping them in good condition or correcting body odors. In some instances, cosmetic compositions may also include health care compositions.

The organosilane (A), or reaction products derived therefrom, is present in the cosmetic composition in conjunction with a cosmetic ingredient (B), optionally in a cosmetically acceptable medium.

Cosmetic ingredients are those ingredients known to be used in cosmetic application. A wide review of such ingredients may be found in the CTFA cosmetic ingredient handbook.

Cosmetically acceptable medium include water, solvents, diluents, or mixtures and emulsions thereof.

Cosmetic applications include skin care, hair care, or nail care applications.

Cosmetic ingredients include emollients, waxes, moisturizers, surface active materials such as surfactants or detergents or emulsifiers, thickeners, water phase stabilizing agents, pH controlling agents, preservatives and cosmetic biocides, sebum absorbants or sebum control agents, vegetable or botanical extracts, vitamins, proteins or amino-acids and their derivatives, pigments, colorants, fillers, silicone conditioning agents, cationic conditioning agents, UV absorbers, sunscreen agents, antidandruff agents, antiperspirant agents, deodorant agents, skin protectants, hair dyes, nail care ingredients, fragrances or perfume, antioxidants, oxidizing agents, reducing agents, propellant gases, and mixtures thereof.

Additional ingredients that may be used in the cosmetic compositions include fatty alcohols, colour care additives, anticellulites, pearlising agents, chelating agents, film formers, styling agents, ceramides, suspending agents and others.

Health care ingredients include antiacne agents, antibacterial agents, antifungal agents, therapeutic active agents, external analgesics, skin bleaching agents, anti-cancer agents, diuretics, agents for treating gastric and duodenal ulcers, proteolytic enzymes, antihistamine or H1 histamine blockers, sedatives, bronchodilators, diluents.

Additional ingredients that may be used in the health care compositions include antibiotic, antiseptic, antibacterial, antiinflammatory, astringents, hormones, smoking cessation compositions, cardiovascular, antiarrythmic, alpha-I blocker, beta blocker, ACE inhibitor, antiaggregant, non-steroidal anti-inflammatory agents such as diclofenac, antipsoriasis agents such as clobetasol propionate, antidermatitis agents, tranquillizer, anticonvulsant, anticoagulant agents, healing factors, cell growth nutrients, peptides, corticosteroidal drugs, antipruritic agents and others.

Cosmetic ingredients may be used in health care compositions, such as waxes, and others; and health care ingredients may be used in cosmetic compositions such as anti-acne agents, and others.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as C30-45 Alkyl Methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched C8-C16 esters; isohexyl neopentanoate; ester oils such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Example of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, C30-45 alkyldimethylsilyl polypropylsilsesquioxane), and mixtures thereof Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic or non ionic, and include organomodified silicones such as dimethicone copolyol; oxyethylenated and/or oxypropylenated ethers of glycerol; oxyethylenated and/or oxypropylenated ethers of fatty alcohols such as ceteareth-30, C12-15 pareth-7; fatty acid esters of polyethylene glycol such as PEG-50 stearate, PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof.

Further examples of nonionic surfactants include polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, ginkgo biloba, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon or palm. Examples of herbal extracts include dill, horseradish, oats, neem, beet, broccoli, tea, pumpkin, soybean, barley, walnut, flax, ginseng, poppy, avocado, pea, sesame, and mixtures thereof.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate (vitamin A palmitate), retinyl acetate (vitamin A acetate), retinyl linoleate (vitamin A linoleate), and retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolyzed form and they may also be quaternized, such as hydrolyzed elastin, hydrolyzed wheat powder, hydrolyzed silk. Examples of protein include enzymes such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc, and mixtures thereof.

Examples of fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be crosslinked, copolymer microspheres, polytrap, silicone resin microbeads, and mixtures thereof. The fillers may be surface treated to modify affinity or compatibility with remaining ingredients.

Examples of silicone conditioning agents include silicone oils such as dimethicone; silicone gums such as dimethicol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/ glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives, quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl Methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of antidandruff agents include pyridinethione salts, selenium compounds such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants are allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2- methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; Haematoxylon brasiletto wood extract; HC dyes; Lawsonia inermis (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl C21-22 isoalkyl acidate; isatin; Isatis tinctoria leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Example of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; Cetraria islandica extract; Chondrus crispus; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume ingredients are described in detail in standard textbook references such as *Perfume and Flavour Chemicals,* 1969, S. Arctander, Montclair, N.J.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, Camellia sinensis Oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (Melaleuca aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

Examples of antiacne agents include salicylic acid, sulfur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of therapeutic active agents include penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, benzocaine, sulphonamides, ticonazole, perbuterol, furosamide, prazosin, hormones, prostaglandins, carbenicillin, salbutamol, haloperidol, suramin, indomethicane, diclofenac, glafenine, dipyridamole, theophylline, hydrocortisone, steroids, scopolamine, and mixtures thereof.

Examples of external analgesics are benzyl alcohol, capsicum oleoresin (Capsicum frutescens oleoresin), methyl salicylate, camphor, phenol, capsaicin, juniper tar (Juniperus oxycedrus tar), phenolate sodium (sodium phenoxide), capsicum (Capsicum frutescens), menthol, resorcinol, methyl nicotinate, turpentine oil (turpentine), and mixtures thereof.

An example of a skin bleaching agent is hydroquinone.

Examples of anti-cancer agents include alkylating agents (such as busulfan, fluorodopan), antimitotic agents (such as colchicine, rhizoxin), topoisomerase I inhibitors (such as camptothecin and its derivatives), topoisomerase II inhibitors (such as menogaril, amonafide), RNA/DNA or DNA anti-metabolites (such as acivicin, guuanazole), plant alkaloids and terpenoids, antineoplastics, some plant-derived compounds (such as podophyllotoxin, vinca alkaloids), and mixtures thereof.

Examples of diuretics include loop diuretics (such as bumetanide, furosemide), thiazide diuretics (such as chlorothiazide, hydroflumethiazide), potassium-sparing diuretics (such as amioloride, spironolactone), carbonic anhydrase inhibitors (such as acetazolamide), osmotic diuretics (such as mannitol), and mixtures thereof.

Examples of agents for treating gastric and duodenal ulcers include proton pump inhibitor (such as lansoprazole, omeprazole), acid blockers or H2 histamine blockers (such as cimetidine, ranitidine), bismuth, sucralfate, and mixtures thereof.

Examples of proteolytic enzymes include nattokinase, serratiopeptidase, bromelain, papain, and mixtures thereof.

Examples of antihistamine or H1 histamine blockers include brompheniramine, clemastine, cetirizine, loratadine, fexofenadine, and mixtures thereof.

Examples of sedatives include barbiturates (such as phenobarbitol), benzodiazepines (such as lorazepam), herbal sedatives, benzodiazepine-like drugs (such as zolpidem, zopiclone), and mixtures thereof.

Examples of bronchodilators include short-acting β2-agonists and long-acting β2-agonists, anticholinergics, and mixtures thereof.

The formulations of the present invention also include diluents. Such diluents are often necessary to decrease the viscosity of the formulation sufficiently for application.

Examples of diluents include silicon containing diluents such as hexamethyldisiloxane, octamethyltrisiloxane, and other short chain linear siloxanes such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes such as hexamethylcyclotrisiloxane, octamethylcyclotetrasiloxane, decamethylcyclopentasiloxane, dodecamethylcyclohexasiloxane; organic diluents such as butyl acetate, alkanes, alcohols, ketones, esters, ethers, glycols, glycol ethers, hydrofluorocarbons or any other material which can dilute the formulation without adversely affecting any of the component materials of the cosmetic composition. Hydrocarbons include isododecane, isohexadecane, Isopar L (C11-C13), Isopar H (C11-C12), hydrogenated polydecene. Ethers and esters include isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols.

Further materials suitable for the personal care and health care are well known to the person skilled in the art and are described in many text books as well as other publications.

The general level of organosilane (A) in the cosmetic compositions may vary from 0.01% to 20% by weight, alternatively from 0.05% to 10%, alternatively from 0.1% to 5%, relative to the total weight of the cosmetic composition. The cosmetic ingredient (B) is present at a level of from 0.01% to 99.99% by weight, relative to the total weight of the cosmetic composition. The cosmetic ingredient (B) may be a mixture of cosmetic ingredients (B) as listed above.

The cosmetic composition may be prepared by a process comprising the steps of
i. Mixing an organosilane (A) having the formula;

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group
ii. with at least one cosmetic ingredient (B)
iii. optionally in the presence of a cosmetically acceptable medium.

The process may be conducted at temperatures ranging of from 15 to 90° C., alternatively of from 20 to 60° C., alternatively at room temperature (25° C.), using simple propeller mixers, Brookfield counter-rotating mixers, or homogenizing mixers. No special equipment or processing conditions are typically required. Depending on the type of composition prepared, the method of preparation will be different, but such methods are well known in the art.

The cosmetic compositions may be in the form of a cream, a gel, a powder (free flowing powder or pressed), a paste, a solid, freely pourable liquid, an aerosol. The cosmetic compositions may be in the form of monophasic systems, biphasic or alternate multi phasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone.

Skin care compositions include shower gels, soaps, hydrogels, creams, lotions and balms; antiperspirants; deodorants such as sticks, soft solid, roll on, aerosol, and pumpsprays; skin creams; skin care lotions; moisturizers; facial treatments such as wrinkle control or diminishment treatments; exfoliates; body and facial cleansers; bath oils; perfumes; colognes; sachets; sunscreens; mousses; patches; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof.

Hair care compositions include shampoos, rinse-off conditioners, leave-in conditioners and styling aids, gels, sprays, pomades, mousses, waxes, cuticle coats, hair colorants, hair relaxants, hair straighteners, permanents, and kits thereof.

Nail care compositions include color coats, base coats, nail hardeners, and kits thereof.

Health care compositions may be in the form of ointments, creams, gels, mousses, pastes, patches, spray on bandages, foams and/or aerosols or the like, medicament creams, pastes or sprays including anti-acne, dental hygienic, antibiotic, healing promotive, which may be preventative and/or therapeutic medicaments, and kits thereof.

The cosmetic compositions may be used by the standard methods, such as applying them to the human or animal body, e.g. skin or hair, using applicators, brushes, applying by hand, pouring them and/or possibly rubbing or massaging the composition onto or into the body. Removal methods, for example for colour cosmetics are also well known standard methods, including washing, wiping, peeling and the like.

The invention also comprises a method of treating hair or skin by applying to it a cosmetic composition according to the first aspect of the invention.

The cosmetic compositions may be used on hair in a conventional manner. An effective amount of the composition for conditioning hair is applied to the hair. Such effective amounts generally range from about 1 g to about 50 g, preferably from about 1 g to about 20 g. Application to the hair typically includes working the cosmetic composition through the hair such that most or all of the hair is contacted with the cosmetic composition. This method for conditioning the hair comprises the steps of applying an effective amount of the hair care composition to the hair, and then working the composition through the hair. These steps can be repeated as many times as desired to achieve the desired conditioning benefit.

Benefits obtained from using the cosmetic compositions on hair include one or more of the following benefits: hair conditioning, softness, detangling ease, silicone deposition, anti-static, anti-frizz, lubricity, shine, strengthening, viscosity, tactile, wet combing, dry combing, improvement in coloration process, color retention, straightening, heat protection, styling, or curl retention.

For example, a process to color keratinous fibers comprises the steps of
i. Mixing an organosilane (A) having the formula;

$$(R^1)_{(3-n)}(R^2O)_n SiR^3O(CH_2CH_2O)_a(C_3H_6O)_b R^4$$

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group
with at least one cosmetic ingredient (B) selected from hair dyes, hair colorants, optionally in the presence of a cosmetically acceptable medium,
ii. Applying the mixture to the keratinous fibers;
iii. Optionally let the mixture stand on the keratinous fibers;
iv. Optionally rinsing the keratinous fibers.

The optional standing time of the process to color keratinous fibers may range of from 10 seconds to 2 hours, alternatively of from 1 minute to 45 minutes, alternatively of from 5 minute to 30 minutes. The process to color keratinous fibers may include the steps of heating, or covering the keratinous substrates during the standing time to reach more intense and deep color of the keratinous fiber.

As further example, a process to maintain color to keratinous fibers comprises the steps of
i. Mixing an organosilane (A) having the formula;

$$(R^1)_{(3-n)}(R^2O)_n SiR^3O(CH_2CH_2O)_a(C_3H_6O)_b R^4$$

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group
with at least one cosmetic ingredient (B) selected from surfactants, hair dyes, hair colorants, optionally in the presence of a cosmetically acceptable medium;
ii. Applying the mixture to the keratinous fibers;
iii. Optionally let the mixture stand on the keratinous fibers;
iv. Optionally rinsing the keratinous fibers.

The optional standing time of the process to maintain color to keratinous fibers may range of from 10 seconds to 2 hours, alternatively of from 1 minute to 45 minutes, alternatively of from 5 minute to 30 minutes. The process to maintain color to keratinous fibers may include the steps of heating, or covering the keratinous substrates during the standing time to reach more intense and deep color of the keratinous fiber.

In a further example of conditioning hair, a process to reduce frizzing of keratinous fibers comprises the steps of
i. Mixing an organosilane (A) having the formula;

$$(R^1)_{(3-n)}(R^2O)_n SiR^3O(CH_2CH_2O)_a(C_3H_6O)_b R^4$$

where
n is 1, 2, or 3,
a≥1, b may vary from 0 to 30, with the proviso a≥b,
$R^1$ is a hydrocarbon group containing 1 to 12 carbon atoms,
$R^2$ is hydrogen or an alkyl group containing 1 to 6 carbon atoms,
$R^3$ is a divalent hydrocarbon group containing 2 to 12 carbon atoms,
$R^4$ is hydrogen, $R^1$, or an acetyl group
with water;
ii. applying the mixture to the keratinous fibers,
iii. optionally letting the mixture stand on the keratinous fibers,
iv. optionally rinsing the keratinous fibers.

The cosmetic compositions may be used on skin in a conventional manner. An effective amount of the composition for the purpose is applied to the skin. Such effective amounts generally range from about 1 mg/cm2 to about 3 mg/cm2. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: skin softness, suppleness, moisturization, skin feel, foam generation.

For example, a process for hydrating skin comprises the steps of
 i. Mixing an organosilane (A) having the formula;

where n is 1, 2, or 3,
a≥1, b may vary from 0 to 30, with the proviso a≥b,
R1 is a hydrocarbon group containing 1 to 12 carbon atoms,
R2 is hydrogen or an alkyl group containing 1 to 6 carbon atoms,
R3 is a divalent hydrocarbon group containing 2 to 12 carbon atoms,
R4 is hydrogen, R1, or an acetyl group
with at least one cosmetic ingredient (B), optionally in the presence of a cosmetically acceptable medium
 ii. and applying it to the skin
 iii. and optionally rinsing the skin.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Example 1

Preparation of Poly (EO) Methyl 3-(Methyldiethoxysilyl) Propyl Ether

PG SF-Allyl EO7-Me (463.73 g; UNIOX MUS-4 from NOF Corporation) and sodium acetate (0.05 g; from Fisher Biotech) were loaded in a 2 L 3-necked round-bottomed flask (RBF) fitted with a crescent-shaped paddle stirring rod, a Claisen adaptor itself fitted with a water cooled condenser and a 250 mL additional funnel loaded with methyldiethoxylsilane (136.52 g; from Gelest, Inc), and a thermometer adaptor itself fitted with a thermal couple, all under nitrogen purge. The reaction mixture was heated to 60° C. when 20 wt. % or 28 g of methyldiethoxylsilane was fed in the RBF immediately followed by the addition of 1% Dow Corning® 2-0707 INT catalyst in IPA (~400 µL or 6 ppm). The exotherm observed instantaneously was 18° C. The remaining methyldiethoxylsilane in the additional funnel was being dispensed into the RBF at ~1.21 g/min rate while temperature was set at 80° C. and being maintained below 85° C. throughout the addition. The second charge of 1% Dow Corning® 2-0707 INT catalyst in IPA (~500 µL or 7 ppm) was done after the first hour of silane addition and ~5° C. exotherm was seen. When all methyldiethoxylsilane was in the RBF, the temperature was set at 85° C. set point and the third addition of 1% Dow Corning® 2-0707 INT catalyst in IPA (~500 µL or 7 ppm) was added while no exotherm was observed. The product mixture was then allowed to reflux for another hour for hydrosilylation completion. Once the reaction was determined to be done, residual SiH was measured by IR which was 34 ppm at peak 2150 cm$^{-1}$. On the following day, the Claisen adapter was replaced by a water cooled condenser fitted with a 250 mL round-bottomed flask. The set-up was connected to vacuum for stripping. The product mixture was stripped for 1 h under 10-40 mmHg vacuum pressure at 90° C. The final residual SiH content measured by IR was 4 ppm at 2150 cm$^{-1}$. The final finished product was pressure-filtered on 20 µm sized filter paper to remove sodium acetate.

Example 2

Preparation of Poly (EO) Methyl 3-(Methyldimethoxysilyl) Propyl Ether

PG SF-Allyl EO7-Me (489.378 g; UNIOX MUS-4 from NOF Corporation) and sodium acetate (0.1 g; from Fisher Biotech) were loaded in a 2 L 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (110.622 g), and a thermometer adaptor itself fitted with a thermal couple, all under nitrogen purge. The reaction mixture was heated to 45° C. when 10 wt. % or 11 g of Z-6701 silane was fed in the RBF immediately followed by the addition of 1% Dow Corning® 2-0707 INT catalyst in IPA (~400 µL or 6 ppm). The exotherm observed instantaneously was 2-3° C. The remaining Z-6701 in the additional funnel was being dispensed into the RBF at ~1.67 g/min rate while temperature set at 53° C. plus 2° C. exotherm was maintained throughout the addition. When all Z-6701 was in the RBF, the temperature of mixture dropped back to the 53° C. set point and hence, there was a second addition of 1% Dow Corning® 2-0707 INT catalyst in IPA (~500 µL or 7 ppm). The mixture was then held for another 2 h to allow reaction gone for completion in which the third addition of 1% Dow Corning® 2-0707 INT catalyst in IPA (~500 µL or 7 ppm) were made after the first hour of reflux. A constant 2° C. exotherm was observed after each time the catalyst was added and had lasted for 1 h except for the last addition which lasted only 30 minutes. Once the reaction was determined to be done, residual SiH was measured by IR which was 35 ppm at peak 2150 cm$^{-1}$. On the following day, the Claisen adapter was replaced by a water cooled condenser fitted with a 250 mL round-bottomed flask. The set-up was connected to vacuum for stripping. The product mixture was stripped for 1 h under 10-20 mmHg vacuum pressure at 60° C. The final residual SiH content measured by IR was 4 ppm at 2150 cm$^{-1}$. The final finished product was pressure-filtered on 20 µm sized filter paper to remove sodium acetate.

Example 3

Preparation of Poly (EO) Hydroxyl 3-(Methyldiethoxysilyl) Propyl Ether

PG SF-Allyl EO7-OH (191.85 g; from Dow Chemical Company) and sodium acetate (0.05 g; from Fisher Biotech) were loaded in a 500 mL 3-necked round-bottomed flask (RBF) fitted with a crescent-shaped paddle stirring rod, a Claisen adaptor itself fitted with a water cooled condenser and a 250 mL additional funnel loaded with methyldiethoxylsilane (58.67 g from Gelest, Inc), and a thermometer adaptor itself fitted with a thermal couple, all under nitrogen purge. The reaction mixture was heated to 60° C. when 10 wt. % or 6 g of methyldiethoxylsilane was dispensed in the RBF immediately followed by the addition of 1% Dow Corning® 2-0707 INT catalyst in IPA (~230 μL or 8 ppm). The exotherm observed instantaneously was 7° C. The remaining methyldiethoxylsilane in the additional funnel was being dispensed into the RBF at ~0.88 g/min rate while temperature was set at 67° C. and being maintained at ~75° C. throughout the addition. When all methyldiethoxylsilane was added to the RBF, the temperature was set at 75° C. to reflux for an hour to allow the reaction to go to completion. The reaction mixture was cooled down to 60° C. and 159 ppm of residual SiH was obtained by IR at peak 2150 cm$^{-1}$. A second addition of 1% Dow Corning® 2-0707 INT catalyst in IPA (~50 μL or ~1.7 ppm) was charged to the reaction mixture, however, no exotherm was detected. The reaction temperature was increased to 80° C. and refluxed for an hour. The residual SiH was measured 126 ppm. On the following day, the product mixture was transferred to a 1 L round-bottomed flask for rotary evaporation. Some material was stripped out while the vacuum pressure was at ~3-4 mmHg and the water bath was at 80° C. This process lasted for two hour and the final product has 13 ppm of SiH left. The final product was pressure-filtered on 20 μm filter paper to remove sodium acetate.

Example 4

Preparation of Poly (EO) Hydroxyl 3-(Methyldimethoxysilyl) Propyl Ether

PG SF-Allyl EO7-OH (80.58 g; from Dow Chemical Company) and sodium acetate (0.03 g; from Fisher Biotech) were loaded in a 250 mL 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (20.06 g), and a thermometer adaptor itself fitted with a thermal couple, all under nitrogen purge. The reaction mixture was heated to 45.6° C. when 10 wt. % or 2 g of Dow Corning® Z-6701 Silane was dispensed in the RBF immediately followed by the addition of 1% Dow Corning® 2-0707 INT catalyst in IPA (~60 μL or 5 ppm). The exotherm observed instantaneously was 0.9° C. The remaining Dow Corning® Z-6701 Silane in the additional funnel was being dispensed into the RBF at ~0.21 g/min rate while temperature was set at 50° C. and being maintained at ~49-51° C. throughout the addition. When all methyldiethoxylsilane was added to the RBF, the temperature was set at 57° C. to reflux for 2.5 hours to allow reaction gone for completion. The reaction mixture was cooled down to room temperature and 121 ppm of residual SiH was obtained by IR at peak 2150 cm$^{-1}$. On the following day, extra PG SF-Allyl EO7-OH (5.48 g from Dow Chemical Company) was added to the reaction mixture while holding the reaction at 57±1° C. for 4.5 h, resulting in 20 ppm residual SiH. The Claisen adapter was replaced by a water cooled condenser fitted with a 250 mL round-bottomed flask the day after. The set-up was connected to vacuum for stripping. The product mixture was stripped for 3 h under 10-50 mmHg vacuum pressure at 80° C. The final residual SiH content measured by IR was still 20 ppm at 2150 cm$^{-1}$. The final finished product was pressure-filtered on 20 μm sized filter paper to remove sodium acetate.

Example 5

Preparation of Poly (EO) Acetate 3-(Methyldimethoxysilyl) Propyl Ether

PG SF-Allyl EO7-Ac (247.77 g) and sodium acetate (0.05 g from Fisher Biotech) were loaded in a 500 mL 3-necked round-bottomed flask (RBF) fitted with a crescent-shaped paddle stirring rod, a Claisen adaptor itself fitted with a water cooled condenser and a 250 mL additional funnel loaded with Dow Corning® Z-6701 Silane (52.98 g), and a thermometer adaptor itself fitted with a thermal couple, all under nitrogen purge. The reaction mixture was heated to 47° C. when 10 wt. % or 5 g of Dow Corning® Z-6701 Silane was dispensed in the RBF immediately followed by the addition of 1% Dow Corning® 2-0707 INT catalyst in IPA (~270 μL or 8 ppm). The exotherm observed instantaneously was 1-2° C. The remaining Dow Corning® Z-6701 Silane in the additional funnel was being dispensed into the RBF at ~0.79 g/min rate while temperature was set at 54° C. and being maintained below 58° C. throughout the addition. When all Dow Corning® Z-6701 Silane was added to the RBF, the temperature was set at 54° C. to reflux for an hour to allow reaction gone for completion. 540 ppm of residual SiH was obtained by IR at peak 2150 cm$^{-1}$. Another hour of reflux was proceeded and the residual SiH was measured 300 ppm. On the following day, the Claisen adapter was replaced by a water cooled condenser fitted with a 250 mL round-bottomed flask. The set-up was connected to vacuum for stripping. The product mixture was stripped for a total of 3 h under 20-80 mmHg vacuum pressure at 62° C. The final residual SiH content measured by IR was 28 ppm at 2150 cm$^{-1}$. The final finished product was pressure-filtered on 20 μm sized filter paper to remove sodium acetate.

Example 6

To a three neck round bottom flask was added 0.20 g (2.4 mmoles) of sodium acetate and 171.8 g (0.29 moles) of a polyether containing an allyl end, approximately 12 ethylene oxide units and capped with acetate. Next, 28.2 g (0.21 moles) of methyl diethoxy silane (MDES) was added to the flask. With stirring under $N_2$, the mixture was heated to 75°±5° C. and then 3 ppm of Pt catalyst was added. After a small exotherm (<10°±1° C.) the mixture was maintained at 85°±5° C. for 6 hours. At this point the reaction was 98.9% complete as measured by SiH consumption via FTIR. The mixture was stripped of volatiles by heating to 120°±5° C./5-10 mmHg for 4 hours. Finally, the mixture was cooled to room temperature and filtered through Celite that was supported on a Nylon filter to yield 167 g (83% yield) of a light yellow oil. Characterization of this material indicated that the desired product had been obtained as evidenced by the single peak in the $^{29}$Si NMR at approximately −5.6 ppm Example 7

To a three neck round bottom flask was added 0.25 g (3.0 mmoles) of sodium acetate and 189.3 g (97 mmoles) of a polyether containing an allyl end, approximately 18 ethylene oxide units and 18 propylene oxide units and capped with acetate. Next, 10.9 g (81 moles) of methyl diethoxy silane (MDES) was added to the flask. With stirring under $N_2$, the mixture was heated to 75°±5° C. and then 4 ppm of Pt catalyst was added. After a small exotherm (<10°±1° C.) the mixture was maintained at 85°±5° C. for 3 hours. At this point the reaction was 99.6% complete as measured by SiH consumption via FTIR. The mixture was stripped of volatiles by heating to 120°±5° C./5-10 mmHg for 5 hours. Finally, the mixture was cooled to room temperature and filtered through Celite that was supported on a Nylon filter to yield 153 g (76% yield) of a light yellow oil. Characterization of this material indicated that the desired product had been obtained as evidenced by the single peak in the $^{29}$Si NMR at approximately −5.6 ppm.

Example 8

To a three neck round bottom flask was added 0.25 g (3.0 mmoles) of sodium acetate and 168.7 g (0.31 moles) of a polyether containing an allyl end, approximately 12 ethylene oxide units and was not capped. Next, 31.4 g (0.24 moles) of methyl diethoxy silane (MDES) was added to the flask. With stirring under N$_2$, the mixture was heated to 75°±5° C. and then 3 ppm of Pt catalyst was added. After a small exotherm (<10°±1° C.) the mixture was maintained at 85°±5° C. for 3 hours. At this point the reaction was 99.5% complete as measured by SiH consumption via FTIR. The mixture was stripped of volatiles by heating to 120°±5° C./5-10 mmHg for 4 hours. Finally, the mixture was cooled to room temperature and filtered through Celite that was supported on a Nylon filter to yield 149 g (74% yield) of a light yellow oil. Characterization of this material indicated that the desired product had been obtained as evidenced by the single peak in the $^{29}$Si NMR at approximately −5.6 ppm.

Example 9

Hair Care Evaluation for Reducing Frizz

To demonstrate the conditioning ability of the present silane polyethers to reduce frizz, a series of hair conditioning evaluations were conducted on the silane polyether of Example 8 using the following procedures and materials.

Hair tresses were obtained from International Hair Importers and Products, and were thick frizzy, 2.84 g/20 cm net, 1" wide (cut in half to make two 0.5" tresses). All hair tresses were washed in a 9% SLES (sodium lauryl ether sulfate) solution and were then combed through 5 times and were then dried overnight. The tresses were then treated with the test solution by submerging for 10 seconds, making sure that all the hair was wetted. Excess solution was wrung from the tresses and then they were combed through 5 times. Tresses were then laid on a tray and placed in a 40° C. oven for 1 hour to dry. Tresses were the placed in a humidity chamber (25° C., 70% RH). Tresses were compared prior to placing in the humidity chamber and then at t=0, (initial), 30, 60, 120, 180 minutes and after removing from the humidity chamber. Test solutions were 2% of the silane polyether sample of Example 8 in water with the pH adjusted to 4, 7 or 10 with the control being deionized (DI) water. An additional control was ION Lusterizing Cream and the tresses were treated by working in this treatment with fingers and then combing through 5 times and the drying as with the other tresses and then placing in the humidity chamber.

Treated tresses did not feel coated or tacky. Tress treated with water felt the roughest, while the tress treated with silane polyether at pH4 felt the smoothest. The tresses treated with pH7 and pH10 felt similar and better than water, but not as good as pH4.

Tresses treated with the silane polyether of Example 8 (at all pH values) could be combed through in one pass (control could not) and held shape much better than the control. All the tresses treated with the silane polyether (regardless of pH) had much less fizz than the control at all times in and out of the humidity chamber.

Tress treated ION Lusterizing Cream felt the smoothest and slipperiest, followed by the tress treated with the silane polyether. The tress treated with DI water felt roughest. ION treated tress felt coated and left a film on fingers while the tress treated with silane polyether did not. Both treated tresses could be combed through in one pass and both held their shape much better than the tress treated with DI water.

The invention claimed is:

1. A method of hair conditioning to reduce frizzing of hair comprises the steps of
    mixing
    i. a hydrophilic organosilane (A) having the formula:

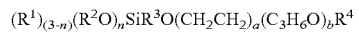

where
        n is 1, 2, or 3,
        a≥1, b is 0 to 30, with the proviso a≥b,
        R$^1$ is a hydrocarbon group containing 1 to 12 carbon atoms,
        R$^2$ is hydrogen or an alkyl group containing 1 to 6 carbon atoms,
        R$^3$ is a divalent hydrocarbon group containing 2 to 12 carbon atoms,
        R$^4$ is hydrogen, R$^1$, or an acetyl group
    with water, thereby forming a mixture; and
    ii. applying the of mixture to the hair;
    iii. optionally letting the mixture stand on the hair for a standing time of from 10 seconds to 2 hours; and
    iv. optionally rinsing the hair.

2. A method according to claim 1 where n is 2.

3. A method according to claim 1 where a ranges from 4 to 30.

4. A method according to claim 2 where a ranges from 4 to 30.

5. A method according to claim 1 where R$^1$ is methyl and R$^2$ is methyl or ethyl.

6. A method according to claim 4 where R$^1$ is methyl and R$^2$ is methyl or ethyl.

7. A method according to claim 1 where R$^3$ is propylene or —CH$_2$CH$_2$C(CH$_3$)$_2$—.

8. A method according to claim 6 where R$^3$ is propylene or —CH$_2$CH$_2$C(CH$_3$)$_2$—.

9. A method according to claim 1 where organosilane (A) has the formula: (CH$_3$)(CH$_3$CH$_2$O)$_2$Si CH$_2$CH$_2$CH$_2$O (CH$_2$CH$_2$O)$_{(a')}$CH$_3$, wherein a' may vary from 4 to 30 and has an average value of 7.

10. A method according to claim 1 where organosilane (A) has the following formula: (CH$_3$)(CH$_3$O)$_2$Si CH$_2$CH$_2$C (CH$_3$)$_2$ O(CH$_2$CH$_2$O)$_{(a'')}$(C$_3$H$_6$O)$_{(b'')}$H, wherein a" may vary from 4 to 30 and has an average value of 18 and b" may vary from 1-30 and has an average value of 18.

11. A method according to claim 1 where the hair care composition of (i) further comprises at least one ingredient selected from emollients, waxes, moisturizers, surface active materials, thickeners, water phase stabilizing agents, pH controlling agents, preservatives, cosmetic biocides, sebum absorbants, sebum control agents, vegetable extracts, botanical extracts, vitamins, proteins, amino-acids and their derivatives, pigments, fillers, silicone conditioning agents, cationic conditioning agents, UV absorbers, sunscreen agents, antioxidants, oxidizing agents, reducing agents, propellant gases, fatty alcohols, pearlising agents, chelating agents, film formers, styling agents, ceramides, suspending agents, or mixtures thereof.

12. A method according to claim 1 wherein (ii) comprises applying 1 to 50 grams of the hair care composition of (i) to the hair.

13. A method according to claim 1 wherein (ii) comprises applying 1 to 20 grams of the hair care composition of (i) to the hair.

\* \* \* \* \*